United States Patent [19]

Ellison

[11] Plant 4,998

[45] Mar. 15, 1983

[54] ASPARAGUS PLANT JERSEY CENTENNIAL

[75] Inventor: J. Howard Ellison, Milltown, N.J.

[73] Assignee: Research Corporation, New York, N.Y.

[21] Appl. No.: 226,779

[22] Filed: Jan. 21, 1981

[51] Int. Cl.[3] ..... A01H 5/00

[52] U.S. Cl. ..... Plt./89

[58] Field of Search ..... Plt./89

[56] References Cited

U.S. PATENT DOCUMENTS

P.P. 4,675 3/1981 Takatori et al. ..... Plt./89

P.P. 4,677 3/1981 Takatori et al. ..... Plt./89

*Primary Examiner*—Robert E. Bagwill

*Attorney, Agent, or Firm*—Frank B. Robb

[57] ABSTRACT

The variety hereof, is particularly outstanding in its wide geographic adaptation, its ability to produce even in areas infested with *Fusarium oxysporum*, better than average rust resistance, with a tolerance also to crown rot (*F. moniliforme*), which is substantially better than comparable varieties and particularly Mary Washington from which the parentage hereof was derived.

2 Drawing Figures

BACKGROUND OF THE INVENTION

This invention relates to a new and distinct variety of asparagus plant which I denominate Jersey Centennial (formerly designated R-M 202 by me) and which is the result of a long period of research on asparagus problems, during which I endeavored to select and produce plants which will provide the basis for suitable hybrids of which the instant variety is probably the most valuable up to the present time.

The problems with asparagus are well known, and in particular in certain areas in New Jersey, where the fields are Fusarium infested, and which have been the site of growth of the Mary Washington variety which is an unpatented variety but which is well known and has been used for years as a basis for asparagus production.

In view of the fact that asparagus production had decreased and that such problems as above suggested did in fact exist, the yield having decreased as a result, it is important to note that the instant variety in all respects is a substantial improvement over the Mary Washington variety which was the basis for the selection of the parents hereof.

The seed parent of this particular hybrid variety was selected for its vigor, in an old cultivated asparagus field in New Jersey and when selected, a substantial portion of the crowns in the field were dead, but this particular crown had large stalks which were healthy and round in cross-section.

The pollen parent was selected some years ago for its rust resistance and vigor from another old cultivated field in New Jersey, and in this instance the parent had a large number of stalks, the largest of three stalks measuring 19, 17 and 16 mm in diameter 2.5 cm above the ground.

By asexual reproduction carried on by me, using the crown division system of propagation, the subject variety was produced ultimately and as time passed and growth was undertaken with the thus produced variety, substantially more large size or jumbo asparagus was produced, in fact substantially 80% more average production and 50% more marketable early season yield than the Mary Washington variety.

It is noted that an important aspect of asparagus production is whether jumbo spears can be produced, which provide higher commercial value than small spears, with the fresh market price even more favorable in early season.

Long time testing of this particular variety indicated a yield of 38% more total weight than the Mary Washington variety, the greatest yield differences having taken place in the later years of production, indicating a good long term yield outlook for Jersey Centennial.

This variety displayed superior stand and vigor in comparison with Mary Washington on Fusarium infested land in south New Jersey, in addition to the experimental site where yield was measured particularly carefully.

It is probable that part of the yield difference between varieties during later years is due to the greater Fusarium tolerance of this variety as compared with Mary Washington.

Experimental trials with the instant variety in Michigan near Sodus, indicate higher marketable yields than other asparagus. While Jersey Centennial was not necessarily the highest yielding initially, in its later period of growth it has surpassed the yield of other varieties and shows steadily increasing ability to produce. During 1977–1979, Jersey Centennial yielded 131% more than Mary Washington, and 169% more than the mean of 7 other cultivars.

| Asparagus Variety | Early Jumbo(1) % | Early Yield(2) % | Total Yield(3) % |
|---|---|---|---|
| Washington | 100 | 100 | 100 |
| Jersey Centennial | 180 | 150 | 138 |

(1)Early (2wk) yield of large 17.8 cm spears 1.6 cm diam.
(2)Early (2wk) yield of marketable 17.8 cm spears 1.0 cm diam.
(3)projected total yield of marketable 17.8 cm spears 1.0 cm diam.

Added distinctive comparison may be made by summarizing the mean relative yield of a number of asparagus varieties in a replicated test over a substantial period at Sodus, Mich. with the following results:

| | Relative Yield, %(1) | |
|---|---|---|
| Asparagus Varieties(1) | All Tests | Latest Tests |
| Jersey Centennial | 124 | 231 |
| Mary Washington | 100 | 100 |
| MSU-1 | 103 | 130 |

-continued

| Asparagus Varieties[1] | Relative Yield, %[1] All Tests | Relative Yield, %[1] Latest Tests |
|---|---|---|
| Cal. 66 | 87 | 66 |
| Cal. 72 | 81 | 53 |
| Cal. 309 | 88 | 131 |
| N.J. Approved | 74 | 53 |
| RH 201 | 76 | 99 |
| Cal. 711 | 67 | 69 |

[1]Marketable pears 1.0 cm diam. and greater.

From this consideration, it will be observed that the instant variety which I term a clonal hybrid, is in fact a substantial improvement over any variety with which I have had contact and for which any information has been assembled.

In summary, my new variety Jersey Centennial does in fact provide rust resistance (to *Puccinia asparagi*), good field tolerance to root rot (*Fusarium oxysporum*) and crown rot (*F. moniliforme*) with accompanying high yield. Further, and perhaps of even greater importance, is the fact that this particular variety exhibits wide geographic adaptation as is evidenced from the fact that growth in New Jersey and in Michigan are fairly comparable.

I have also prepared a table which sets forth some of the important data with regard to this particular hybrid variety with respect to its growing configuration and various aspects of growth including nodal, crown and other dimensional aspects. The drawing supplied, nomenclature appended, discloses a typical plant, the specific aspects being summarized as follows:

| | |
|---|---|
| Number of nodes below first branch | 23.0 |
| Number of cm from Crown to first branch | 61.9 |
| Number of Branches | 50.2 |
| Number of cm between first and last branch | 116.2 |
| Number of Cladophyll nodes beyond last branch | 23.9 |
| Numbeer of cm beyond last branch | 14.4 |
| Diameter (mm) highest headed stalk | 16.7 |
| Diameter (mm) largest stalk | 18.0 |
| Internode length (cm) between branches | 2.31 |
| Internode length (cm) beyond last branch | 0.61 |

While I have found that color is not absolutely distinctive in different asparagus varieties, it is one factor to distinguish the same. The drawing hereof discloses my new variety in a color representation as nearly like that of the actual plant as is possible to make in a color reproduction of this kind with the color reference relating to the stalk being determined from comparison with Munsell Color Cascade published by MacBeth Division of Kolmorgen Corporation, the color being noted where the bloom is removed from the stalk, the color notation being 22-11 yellowish green.

The flowers of the plant may be described as including yellow petal tips notation 24-6, with the green rib of the petal 22-11. The yellow petal tip refers to the blossom ends of the petals, approximately half way to the base. The green rib of the petal refers to the mid rib of the petal which extends from the base to approximately three-fourths the length of the petals. The extreme basal portion of the petals also is the same shade of green.

The instant hybrid, as compared with the Mary Washington variety previously mentioned, differs in several measurable aspects: Specifically the distance from the crown to the first branch, fewer branches than Mary Washington variety with the number of cladophyll nodes beyond the last branch being greater.

The substantially improved rust resistance and good field tolerance to root rot and crown rot with related high yield indicate the outstanding characteristics of this hybrid variety and the invention hereof.

The various dimensional notations in the table previously set forth, are considered in the light of the drawing comprising a part hereof which discloses a typical asparagus plant in which the titles of the notations are disclosed.

I have found that identification of asparagus plants which I have developed, may be materially assisted by using this table and in fact affords a basis for distinguishing my new variety from other similar, even related varieties.

I claim:

1. A new and distinct hybrid variety of asparagus plant substantially as herein shown and described, characterized particularly as to novelty by the unique combination of very substantially increased yield, over prior known varieties, good field tolerance to root rot (*Fusarium oxysporium*) and crown rot (*F. moniliforme*), with decided ability to maintain these characteristics in different geographic areas and still produce similarily with the tolerances and resistance to rust being maintained at those wide spread geographic areas, and the commercially valuable aspects provided thereby.

* * * * *

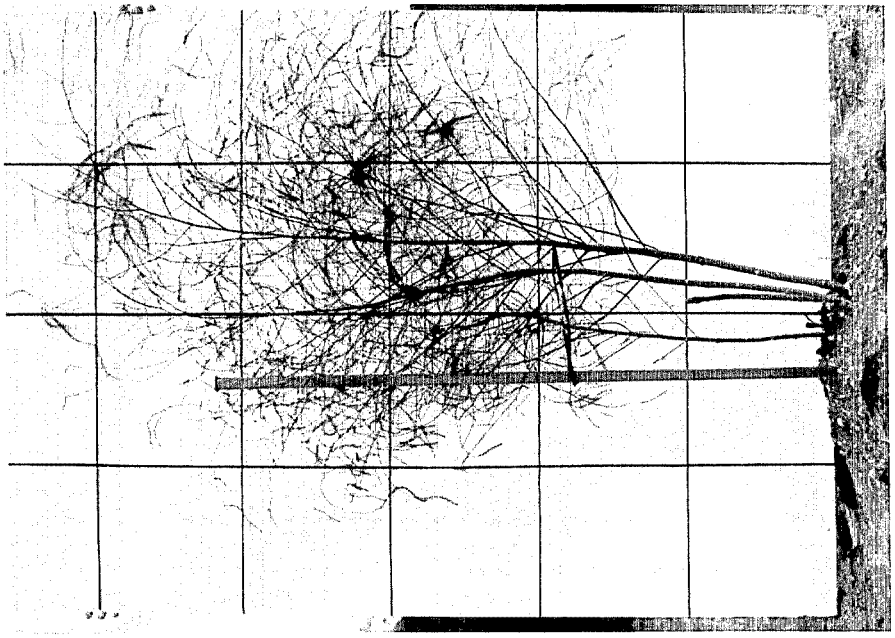
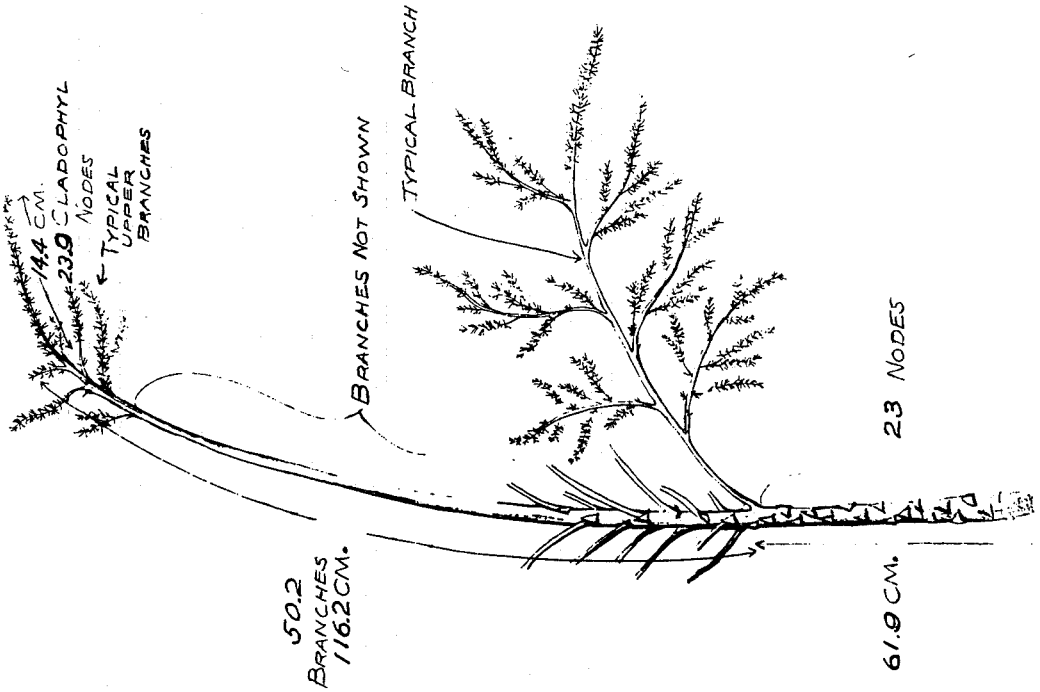
14.4 CM.
23.9 CLADOPHYL NODES
TYPICAL UPPER BRANCHES
BRANCHES NOT SHOWN
TYPICAL BRANCH
50.2 BRANCHES 116.2 CM.
23 NODES
61.9 CM.